United States Patent
Heismann

(10) Patent No.: US 7,643,866 B2
(45) Date of Patent: Jan. 5, 2010

(54) METHOD FOR PRODUCING A COMPUTED TOMOGRAPHY DISPLAY OF TISSUE STRUCTURES BY APPLYING A CONTRAST MEDIUM

(75) Inventor: Bjoern Heismann, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 537 days.

(21) Appl. No.: 11/300,416

(22) Filed: Dec. 15, 2005

(65) Prior Publication Data

US 2006/0134000 A1    Jun. 22, 2006

(30) Foreign Application Priority Data

Dec. 16, 2004   (DE) ................. 10 2004 060 580

(51) Int. Cl.
*A61B 5/05*   (2006.01)
(52) U.S. Cl. ................ 600/425; 600/458; 378/97; 378/98.9
(58) Field of Classification Search ................ None
See application file for complete search history.

(56) References Cited

U.S. PATENT DOCUMENTS

| | | | | |
|---|---|---|---|---|
| 4,104,524 A | * | 8/1978 | Aichinger et al. | 378/97 |
| 4,149,081 A | * | 4/1979 | Seppi | 378/5 |
| 4,247,774 A | * | 1/1981 | Brooks | 250/367 |
| 6,584,338 B1 | * | 6/2003 | Van Muiswinkel | 600/419 |
| 6,690,816 B2 | * | 2/2004 | Aylward et al. | 382/128 |
| 2004/0101088 A1 | | 5/2004 | Sabol et al. | |
| 2004/0223585 A1 | * | 11/2004 | Heismann et al. | 378/54 |

FOREIGN PATENT DOCUMENTS

DE   101 43 131 A1   4/2003

OTHER PUBLICATIONS

B.J.Heismann et al.. ,, Density and atomic number measurements with spectral x-ray attenuation method, in: J Appl Phys, 2003, vol. 94, No. 3, S.2073-2079.

* cited by examiner

*Primary Examiner*—Long V Le
*Assistant Examiner*—Joel F Brutus
(74) *Attorney, Agent, or Firm*—Harness, Dickey & Pierce, P.L.C.

(57) ABSTRACT

A method is disclosed for producing a computed tomography display of tissue structures by applying a contrast medium. A contrast medium is applied to a patient for better visualization of the tissue structure to be examined. An X-ray scan is performed during the presence of the one contrast medium, and computed tomography 2- or 3-dimensional pictures are subsequently reconstructed from the X-ray scan data obtained. In the method, absorption data are measured for at least two different energy spectra, a computed tomography intermediate image is reconstructed per energy spectrum, and the distribution of the one contrast medium in the tissue is determined from the different energy-specific absorption behavior between tissue and contrast medium.

11 Claims, 6 Drawing Sheets

METHOD FOR PRODUCING A COMPUTED TOMOGRAPHY DISPLAY OF TISSUE STRUCTURES BY APPLYING A CONTRAST MEDIUM

The present application hereby claims priority under 35 U.S.C. §119 on German patent application number DE 10 2004 060 580.7 filed Dec. 16, 2004, the entire contents of which is hereby incorporated herein by reference.

FIELD

The invention generally relates to a method for producing a computed tomography display of tissue structures by applying a contrast medium. In at least one embodiment, a contrast medium is applied to a patient for better visualization of the tissue structure to be examined. Further, an X-ray scan is performed during the presence of the one contrast medium, and computed tomography 2- or 3-dimensional pictures subsequently is reconstructed from the X-ray scan data obtained.

BACKGROUND

It is known in principle in computed tomography to apply contrast medium in order to amplify an image contrast, in particular when representing vessel structures, and thereby to produce an improved image contrast such that the tissue structures or vessel structures that are of interest can be displayed pictorially with a higher contrast. As a rule, use is made here mostly of iodine-containing, liquid, chemical compounds that are not without problems with reference to their biological compatibility. As a rule, after such an application of contrast media, the liver values are still raised in the patients thus examined months after the application.

SUMMARY

It an object of at least one embodiment of the invention to find a method for computed tomography display of tissue structures by applying a contrast medium, in the case of which there is the least possible impairment of the patient, that is to say the quantity of contrast medium used is kept as small as possible.

In at least one embodiment, the inventor has realized that it is possible to reduce sharply the quantity of contrast medium required in a CT examination if, when compiling the computer tomography pictures, not only is the integral absorption behavior of the X-rayed tissue measured, but an energy-specific absorption is measured and these spectral data are used to improve contrast.

In accordance with this basic idea, in at least one embodiment, the inventor proposes that the method for producing a computed tomography display of tissue structures by applying a contrast medium, in the case of which a contrast medium is applied to a patient for better visualization of the tissue structure to be examined, and an X-ray scan is performed during the presence of the one contrast medium, computed tomography 2- or 3-dimensional pictures subsequently being reconstructed from the X-ray scan data obtained, is improved to the effect that absorption data are measured for at least two different energy spectra, a computed tomography intermediate image is reconstructed per energy spectrum, and the distribution of the one contrast medium in the tissue is determined from the different energy-specific absorption behavior between tissue and contrast medium.

On the basis of the additionally obtained information of energy-specific absorption in the tissue viewed, including the X-rayed contrast medium, it is now possible to achieve sufficiently high-contrast images with the aid of a substantially lower contrast medium dose, and to determine the contrast medium distribution in the tissue. If there is a somewhat higher dose commitment in this area, its potential damage is largely more than compensated by the lower biological injury owing to a diminished contrast medium concentration.

The inventor also proposes, in at least one embodiment, ascertaining the atomic number distribution in order to determine the contrast medium distribution. With regard to this method, reference is made to the publication entitled "Density and atomic number measurement with spectral x-ray attenuation method", B. J. Heismann, J. Leppert and K. Stierstorfer, JOURNAL OF APPLIED PHYSICS, Volume 94, number 3, Aug. 1, 2003. Reference is also made to a corresponding Laid-Open Specification DE 101 43 131 A1 of the applicant. The entire disclosure content of both documents is hereby incorporated herein the present patent application by reference.

The inventor, in at least one embodiment, also proposes calculating a significancy statement referring to the distribution of the contrast medium from the at least two intermediate images, it being preferred for the significancy statement to consist in a yes/no statement referring to the presence of contrast medium in a specific volume or at a specific location of the patient.

For example, this significancy statement can be calculated by forming the quotient of the intermediate images, or else by a linear combination of the intermediate images.

The inventor also proposes, in at least one embodiment, that in a CT image display, image values with a positive significancy statement referring to the presence of contrast medium at this point obtain a specific, preferably maximum or minimum, image value. Instead of a maximum or minimum image value, it is also possible to use a color value that is preferably not present in the remaining image display. This typically signifies that in a CT display consisting of gray scale values the areas with contrast medium are emphasized by appropriate coloring.

In order to determine the absorption data referring to different energy spectra, it is possible, for example, to use a dedicated radiation source per spectrum. It is particularly easy thereby to generate different bremsstrahlung spectra by using two X-ray sources with a different accelerating voltage. On the other hand, it is also possible to use different materials for the X-ray anode, the intensity maxima typically present in the X-ray spectrum then occurring at different energy values through the use of different materials such that a clear distinction between the spectra is also possible here. Of course, a combination of the two methods can also be used.

Furthermore, it is also particularly advantageous when a combination of anode material and contrast medium is used, the anode material having an intensity maximum in the bremsstrahlung spectrum, and the contrast medium having an absorption maximum in the energy range of the intensity maximum of the bremsstrahlung generated by this anode material. The presence of contrast medium can be detected particularly well with the aid of the increased absorption in this specific energy range by this selection of anode material and contrast medium.

It is also pointed out that a spring focus can be used instead of two separate X-ray sources, it preferably being possible for the spring focus to be equipped respectively with different anode material at the two focal points.

In a further variant of at least one embodiment of the method, the inventor also proposes that a dedicated detector is used per spectrum to determine the absorption data for the at least two different energy spectra. However, it is also possible that to determine the absorption data for the at least two different spectral energies use is made of at least one detector that can resolve the energy spectrum of the detected radiation for at least two different energies. It is thereby possible to determine the energy-specific absorption of the examination object by using a single radiation spectrum and a single detector. An energy-resolving detector can be used to obtain a multiplicity of intermediate images, reconstructed in an energy-specific fashion, and thereby to arrive at even more detailed statements referring to the presence of contrast medium at the location respectively being viewed.

BRIEF DESCRIPTION OF THE DRAWINGS

Additional features and advantages of the invention emerge from the following description of example embodiments with reference to the drawings, it being pointed out that only the elements essential for directly understanding the invention are shown.

Embodiments of the invention are explained in more detail below with the aid of the drawings, use being made of the following reference symbols: 1: computed tomography unit; 2: first X-ray tube/first focus; 3: first detector; 4: second X-ray tube/second focus; 5: second detector; 6: housing; 7: patient; 8: movable patient couch; 9: system axis; 10: arithmetic-logic unit; $Prg_1$-$Prg_n$: program modules; 11: beam cone of the first focus; 12: beam cone of the second focus; 14: anode material of the first focus; 15: anode material of the second focus; 16: filter; a, c, d: constants; B: intermediate image; $E_1$, $E_2$: energy spectrum; I: final image; S: significancy value; S(Ex): detector data of the energy spectrum Ex; $\mu(E1)$, $\mu(E2)$: energy-specific CT image.

In the drawings:

FIG. 1 shows computed tomography with two tubes/detector combinations;

FIG. 2 shows a schematic of a spring focus system having a common detector and different anode materials;

FIG. 3 shows a schematic of a focus/detector combination having two detectors separated by a filter;

FIG. 4 shows two focus/detector combinations having different anode materials, offset by 90°;

FIG. 5 shows a flowchart of the method according to an embodiment of the invention with formation of the quotient from the energy-specific intermediate images for the purpose of determining significancy;

FIG. 6 shows a flowchart of the method according to an embodiment of the invention with formation of the quotient from the energy-specific intermediate images for the purpose of determining significancy;

FIG. 7 shows a flowchart of the method according to an embodiment of the invention with rhoZ windowing for the purpose of determining significancy.

DETAILED DESCRIPTION OF THE EXAMPLE EMBODIMENTS

Figure 1:
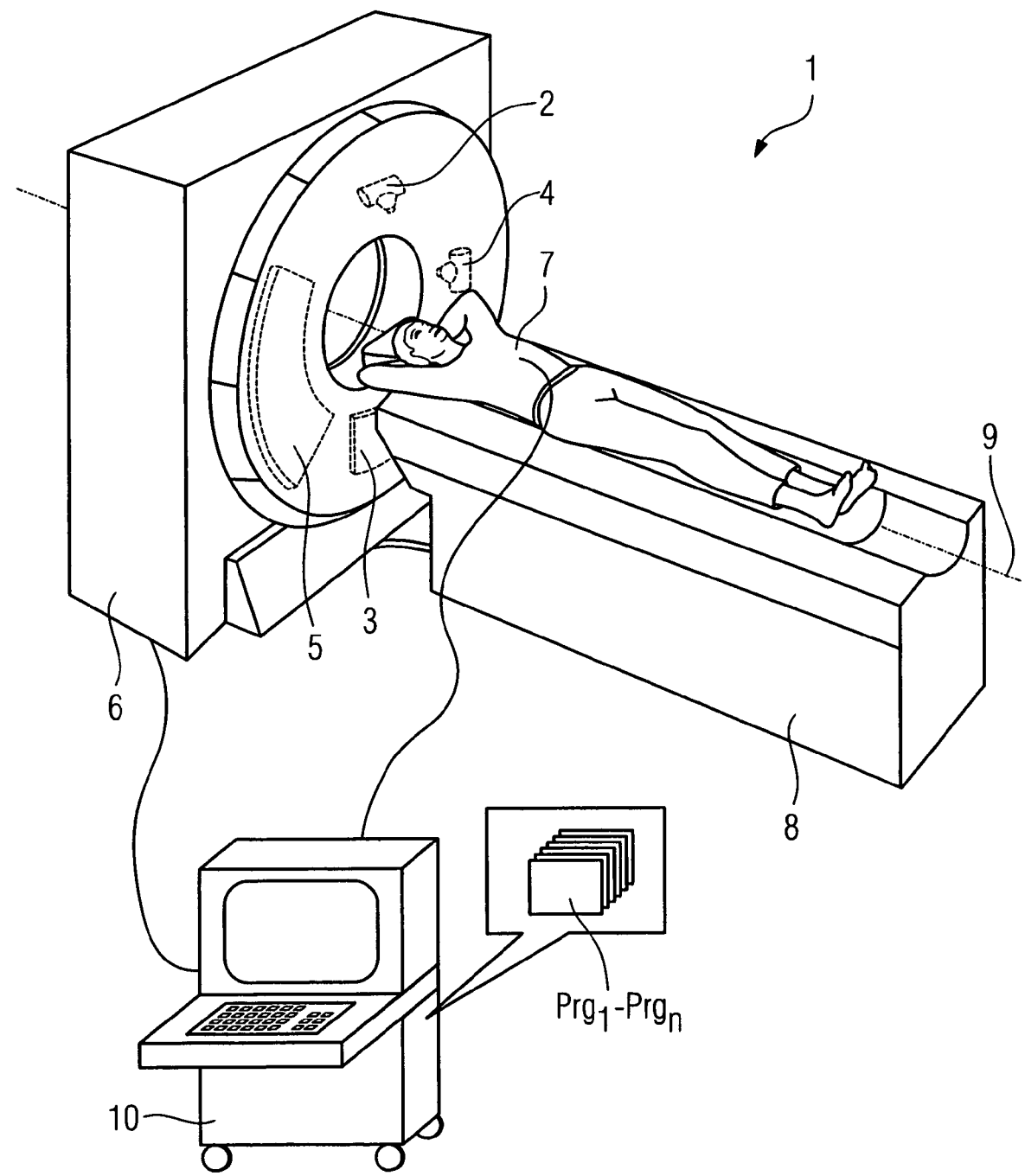

FIG. 1 shows a computed tomography system 1 having a first X-ray tube 2 and a detector 3 assigned to this first X-ray tube 2. Arranged in the gantry in a fashion offset thereto at an angle of 90° is a second focus/detector system having a second X-ray tube 4 and a second detector 5. The patient 7 is located on a movable patient couch 8 that is moved along the system axis 9 during scanning of the patient. The computed tomography system 1 is controlled by the schematically illustrated arithmetic-logic unit 10, the evaluation of the received detector data being carried out by the program modules $Prg_1$ to $Prg_n$.

The double focus/detector combination shown here is only exemplary. It is likewise possible for other variants such as are illustrated schematically by way of example in FIGS. 2 and 4 to be used.

Figure 2:
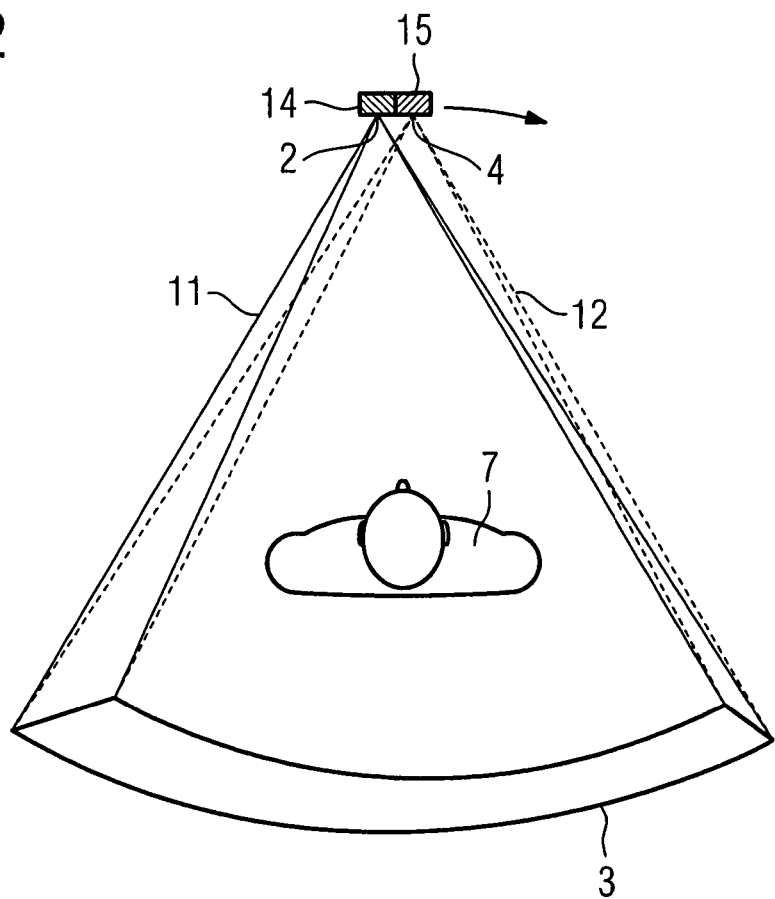

FIG. 2 shows a schematic of a combination composed of a spring focus, including the two foci 2 and 4 that are arranged on different anode materials 14 and 15. Emanating from the foci 2 and 4 are a first beam cone 11 and a second beam cone 12 that impinges on a common detector 3. These two spring foci 2 and 4 can, on the one hand, emit X radiation with different energy spectra owing to their different anode material 14 and 15. In addition, it is also possible when jumping from one focus to the other to switch over to different accelerating voltages such that different bremsstrahlung spectra are generated in addition to the different anode material—or else only thereby.

Figure 3:
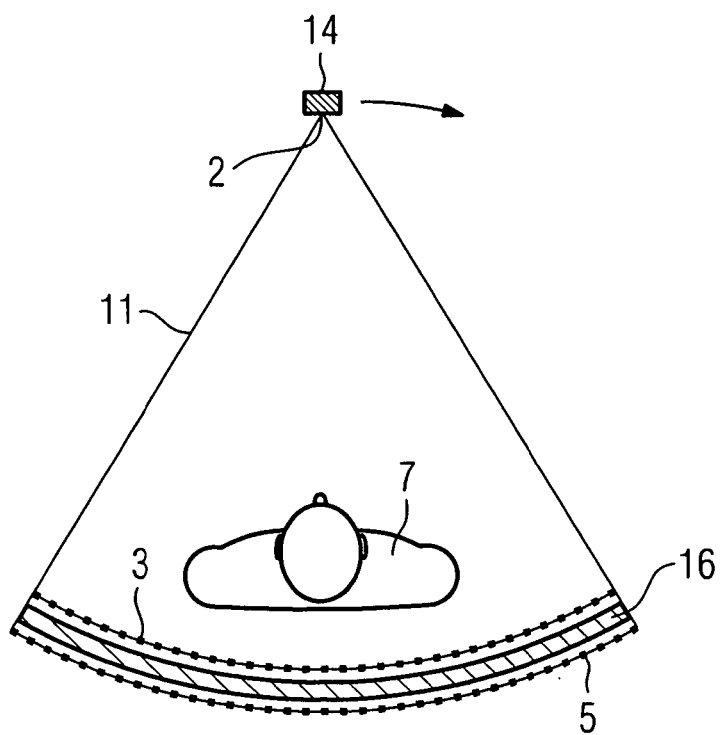

A further variant is illustrated in FIG. 3. Here, a beam 11 that has a typical energy spectrum is generated in a fashion emanating from a common focus 2. This radiation firstly impinges on a first detector 3 in which detector output data with the first energy spectrum are measured. Subsequently, the spectrum experiences filtering by a filter 16 arranged thereunder, and thereafter impinges on the second detector 5 lying thereunder. The filtering filters out the low-energy components of the spectrum such that the second detector 5 detects only the higher-energy components of the X radiation, as a result of which the different absorption of the X-rayed examination object can be established with reference to the different spectral energies.

Figure 4:
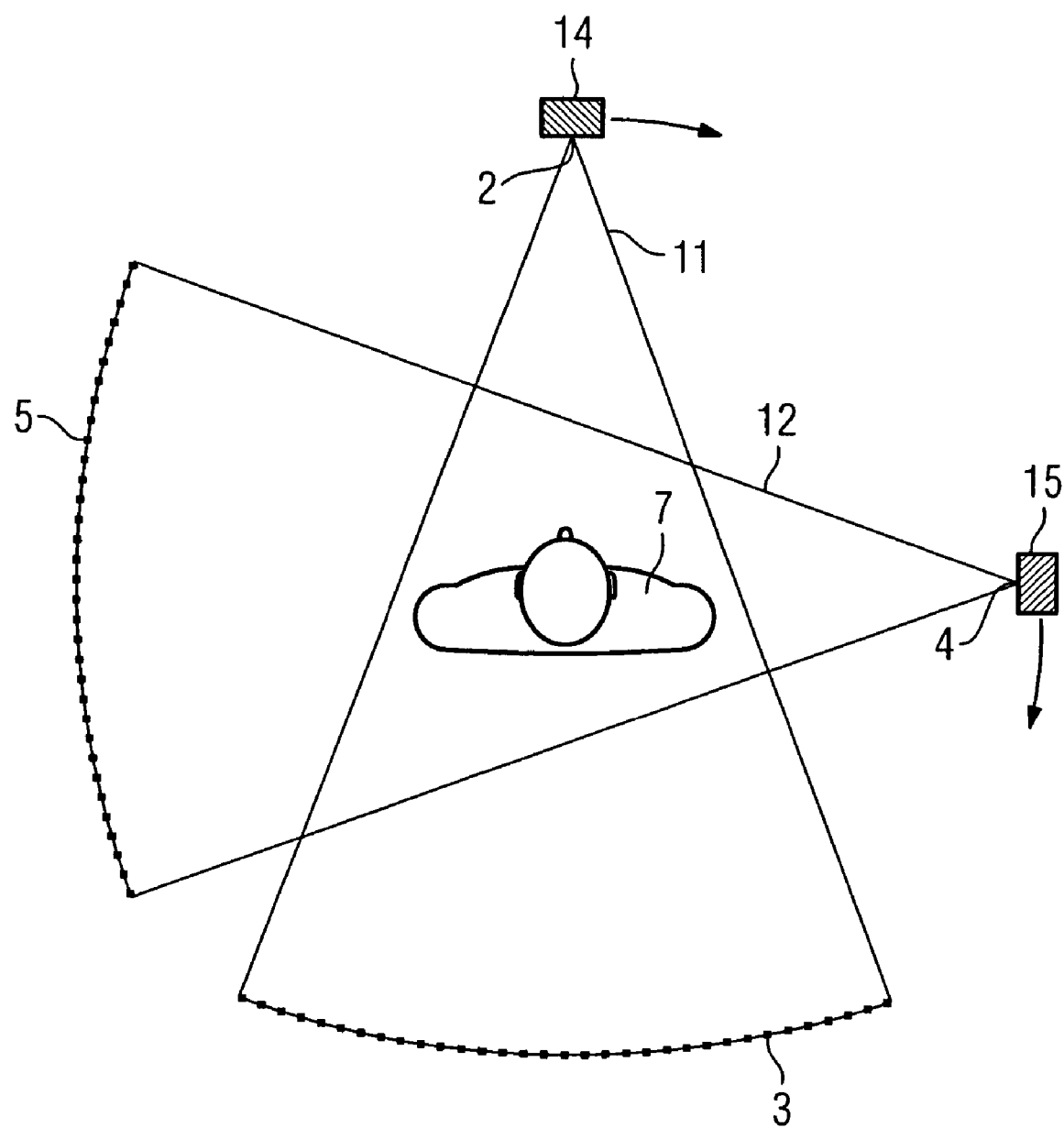

Finally, the double focus/detector combination from FIG. 1 is illustrated schematically again in FIG. 4. Here, work is performed using two different anode materials 14 and 15 and/or different accelerating voltages across the X-ray tubes such that two beam cones 11 and 12 with different energy spectra are produced which are received and evaluated by the detectors 5 and 3 respectively lying opposite one another.

Figure 5:
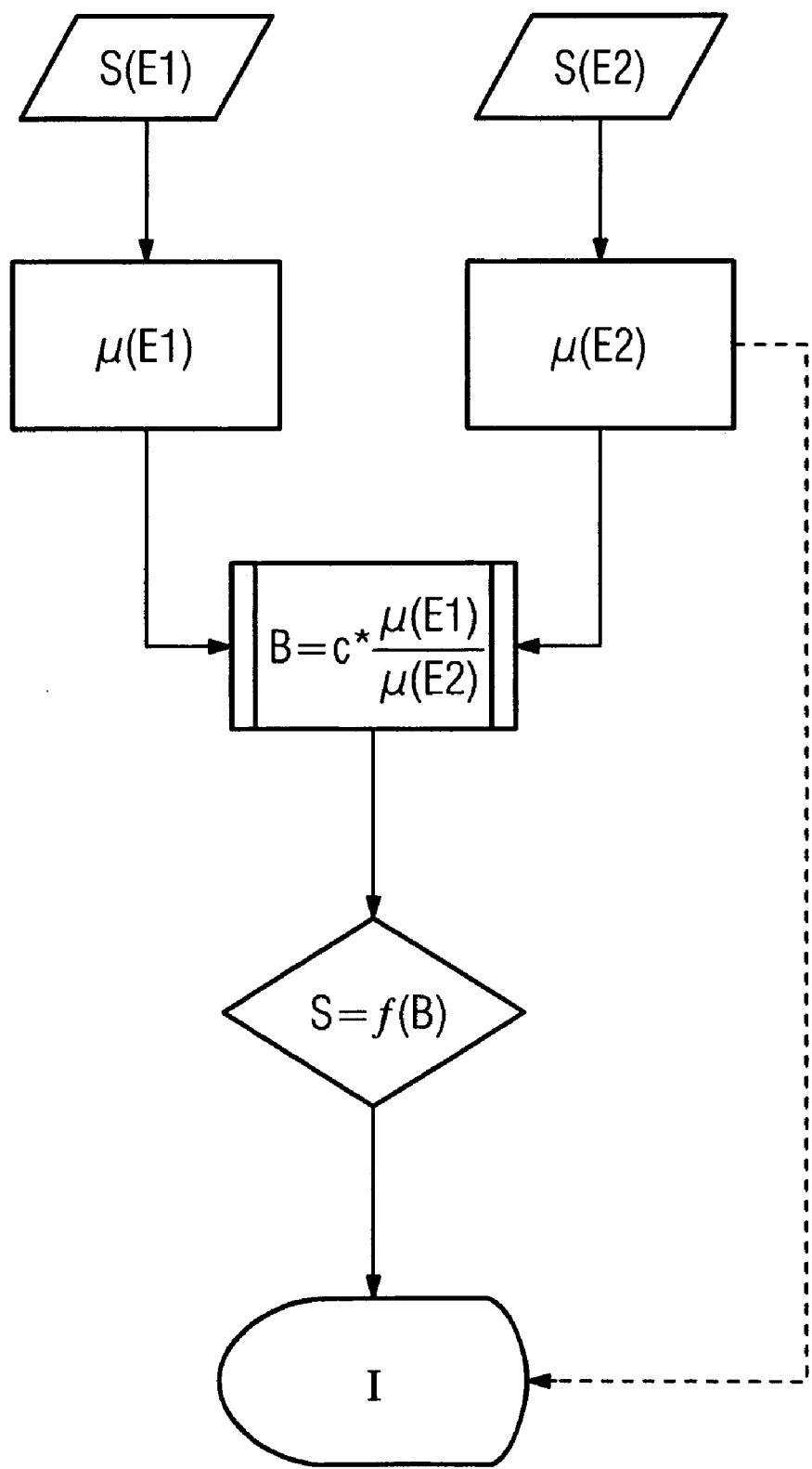

The inventive evaluation of the energy-specific detector data is illustrated schematically in FIGS. 5 to 8. FIG. 5 shows how a scan for the energy-specific detector data S(E1) and S(E2) is firstly carried out for two energy spectra E1 and E2. Subsequently, an energy-specific CT image $\mu(E1)$ and $\mu(E2)$ is calculated for the two energy spectra. An intermediate image B is calculated by forming the quotient of the image values of the energy-specific CT images $\mu(E1)$ and $\mu(E2)$.

Subsequently, it is determined from the respective pixel value or voxel value of the result image B at the location respectively being viewed whether significancy contrast medium is present at this location, and input is made as a significancy value S=f(B), preferably with the aid of the values 0 or 1. In order to display a blood vessel, it now suffices in principle merely to display the significancy values spatially in an image display I.

In addition, a CT display $\mu(E1)$ and/or $\mu(E2)$ can be superimposed on the image display I, it being possible, for example, to undertake a coloring of the normal CT display by using the significancy values 1. Moreover, the bright/dark values present in the CT image can be retained in the coloring.

Figure 6:
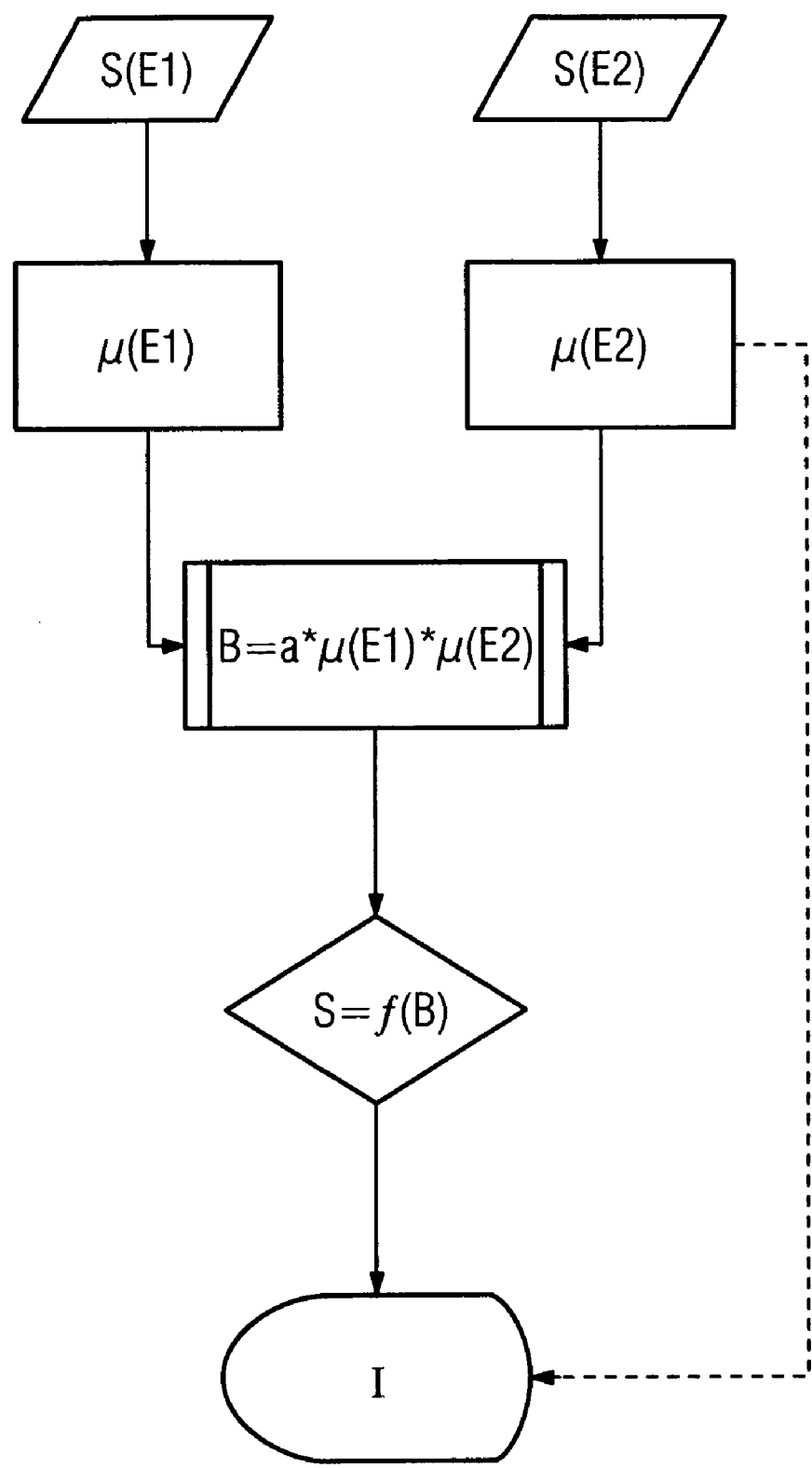
Figure 7:
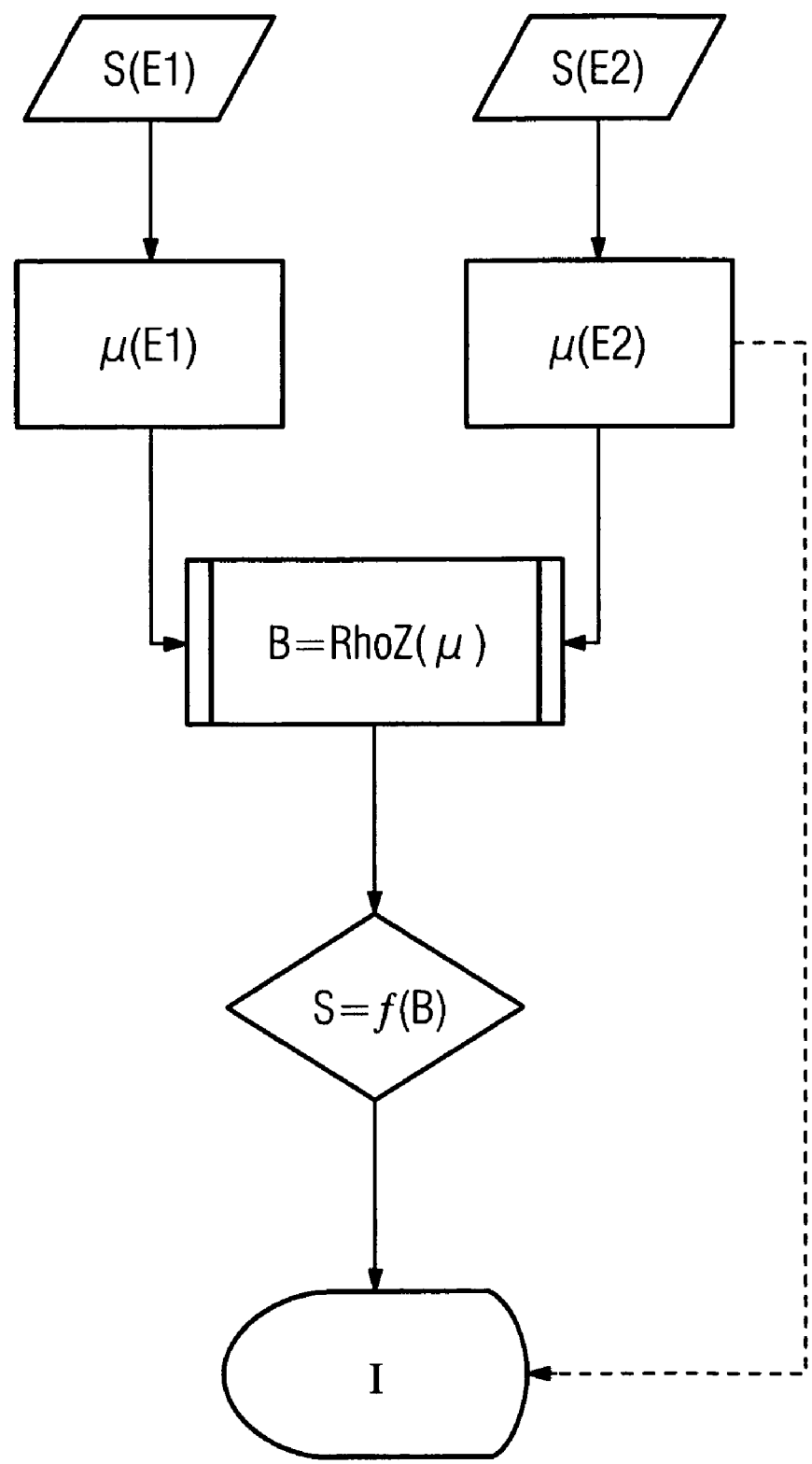

In a way similar to FIG. 5, FIG. 6 shows how, firstly, for two energy spectra E1 and E2 a scan is respectively carried out for the detector data S(E1) and S(E2), and subsequently an energy-specific CT image $\mu(E1)$ and $\mu(E2)$ is calculated for the two energy spectra. This time, the intermediate image B is determined from the product, weighted by the constants a and b, of the energy-specific CT image values of the CT images μ(E1) and μ(E2) at the location, respectively being viewed, of the pixel values or voxel values, and a check is made as to whether significancy contrast medium is present at this location.

Subsequently, the local significance values S=f(B) are determined, preferably with the values 0 or 1. Here, as well, in order to display a blood vessel, it suffices in principle merely to display the significance values S=f(B) spatially in an image display I. In addition, one of the CT displays μ(E1) and/or μ(E2) can likewise be superimposed on the image display I, or the significant points in one of the CT displays can be emphasized.

In a similar way, rhoZ windowing is used to decide on and display the spatial distribution of contrast medium. As illustrated schematically in FIG. 7, here a rhoZ value that constitutes an approximate measure of the atomic number Z of the X-rayed material at the location being viewed is determined from the energy-specific absorption values of the CT images μ(E1) and μ(E2) in accordance with the publications, already named above, entitled "Density and atomic number measurement with spectral x-ray attenuation method", B. J. Heismann, J. Leppert and K. Stierstorfer, JOURNAL OF APPLIED PHYSICS, Volume 94, number 3, Aug. 1, 2003, and DE 101 43 131 A1. If a medium having a mean Z value that is typical and clearly distinguished from the surrounding tissue is selected as contrast medium, it is possible to determine with great reliability the presence of contrast medium at the location being viewed if the rhoZ value falls into a predetermined range, that is to say a value window. In this case, therefore, the significance value 0 or 1 is determined on the basis of the intermediate image B that reflects the spatial distribution of the so-called rhoZ values. The further evaluation and display correspond to the methods from FIGS. 5 and 6.

It is pointed out that the method according to at least one embodiment of the invention is not limited only to determining two energy-specific CT images, but that, in particular given the use of an energy-resolving detector, it is possible to consider a multiplicity of individual energies or energy spectra and to use them for forming the significance values S=f (B).

It is self-evident that the aforementioned features of at least one embodiment of the invention can be used not only in the respectively specified combination but also in other combinations or on their own without departing from the scope of the invention.

Thus, overall, at least one embodiment of the invention exhibits a method for producing a computed tomography display of tissue structures by applying a contrast medium that enables the determination of the contrast medium distribution in a patient by way of an energy-specific reconstruction of CT images of the patient in conjunction with applying very little contrast medium, this being done by considering the energy-specific absorption differences between contrast medium and tissue.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method of determining a distribution of a contrast medium in a tissue structure, an X-ray scan being performed during the presence of the contrast medium, comprising:
    measuring absorption data for at least two different energy spectra;
    reconstructing a computed tomography intermediate image per energy spectrum;
    determining the distribution of the contrast medium in the tissue structure from different energy-specific absorption behavior between the tissue structure and the contrast medium, and
    a calculating significancy statement referring to the distribution of the contrast medium from the at least two intermediate images,
    by forming the quotient of the intermediate images.

2. The method as claimed in claim 1, wherein display image values with a positive significancy statement referring to the presence of contrast medium obtain a predetermined image value in a CT image.

3. The method as claimed in claim 2, wherein the image value is at least one of a maximum and minimum gray scale value.

4. The method as claimed in claim 2, wherein the image value is a color value that is not present in a remaining image display.

5. The method as claimed in claim 1, wherein a dedicated radiation source is used per spectrum to determine the absorption data for the at least two different energy spectra.

6. The method as claimed in claim 1, wherein a dedicated anode material per spectrum is used in the radiation source to determine the absorption data for the at least two different energy spectra.

7. The method as claimed in claim 1, wherein a combination of anode material and contrast medium is used, the anode material having an intensity maximum in an bremsstrahlung spectrum, and the contrast medium having an absorption maximum in an energy range of the intensity maximum of the bremsstrahlung spectrum generated by the anode material.

8. The method as claimed in claim 1, wherein the measuring uses a spring focus.

9. The method as claimed in claim 1, wherein a dedicated detector is used per spectrum to determine the absorption data for the at least two different energy spectra.

10. The method as claimed in claim 1, wherein to determine the absorption data for the at least two different spectral energies, at least one detector that can resolve the energy spectrum of the detected radiation for at least two different energies is used.

11. A method for producing a computer tomography display of a tissue structure by applying a contrast medium, the method comprising:
    applying the contrast medium to a patient for better visualization of the tissue structure to be examined;
    performing an X-ray scan during the presence of the contrast medium;
    measuring absorption data for at least two different energy spectra;
    reconstructing a computed tomography intermediate image per energy spectrum;
    determining the distribution of the contrast medium in the tissue structure from different energy-specific absorption behavior between the tissue structure and the contrast medium;
    reconstructing at least one of computed tomography two-dimensional and-three dimensional pictures, and
    a calculating significancy statement referring to the distribution of the contrast medium from the at least two intermediate images
    by forming the quotient of the intermediate images.

* * * * *